United States Patent [19]
Fumex

[11] Patent Number: 5,989,252
[45] Date of Patent: Nov. 23, 1999

[54] SURGICAL DEVICE FOR ANCHORING IN BONE, AND ANCILLARY FOR INSERTING IT

[76] Inventor: Laurent Fumex, 40 rue des Grands Mourgers, 78730 Saint-Arnoult-En-Yvelinos, France, 78730

[21] Appl. No.: 09/032,943

[22] Filed: Mar. 2, 1998

[30] Foreign Application Priority Data

Feb. 28, 1997 [FR] France ............................. 97 02422

[51] Int. Cl.$^6$ ............................. A61B 17/56; A61F 17/58
[52] U.S. Cl. ............................. 606/72
[58] Field of Search ................... 606/69, 72, 60

[56] References Cited

U.S. PATENT DOCUMENTS

| | | | |
|---|---|---|---|
| 5,217,486 | 6/1993 | Rice et al. | 606/72 |
| 5,443,482 | 8/1995 | Stone et al. | 606/232 |
| 5,465,731 | 11/1995 | Bell et al. | 600/37 |

FOREIGN PATENT DOCUMENTS

WO 95/32669  12/1995  WIPO .

OTHER PUBLICATIONS

F. Alan Barber, MD, Morley A. Herbert, PhD., James N. Click, PA–C; "The Ultimate Strength of Suture Anchors", Arthroscopy: The Journal of Arthroscopic and Related Surgery, vol. 11, No. 1 (Feb.), 1995; pp. 21–28.

*Primary Examiner*—Michael Buiz
*Assistant Examiner*—Vy Q. Bui
*Attorney, Agent, or Firm*—Burns, Doane, Swecker & Mathis, L.L.P.

[57] ABSTRACT

A surgical device suitable for anchorage of a thread or wire to a bone having a hole bored therein. The device includes a thread or wire in the form of a loop having a running knot. The thread or wire carries a deformable tubular sleeve which slides along the thread or wire within the limits of the loop. Also, there is provided an ancillary for inserting the anchoring device. The ancillary includes a shaft suitable for introduction into the hole bored in the bone, which at one end has a spike that can hold the loop of thread or wire, and at the other end has a handle for manipulation.

12 Claims, 7 Drawing Sheets

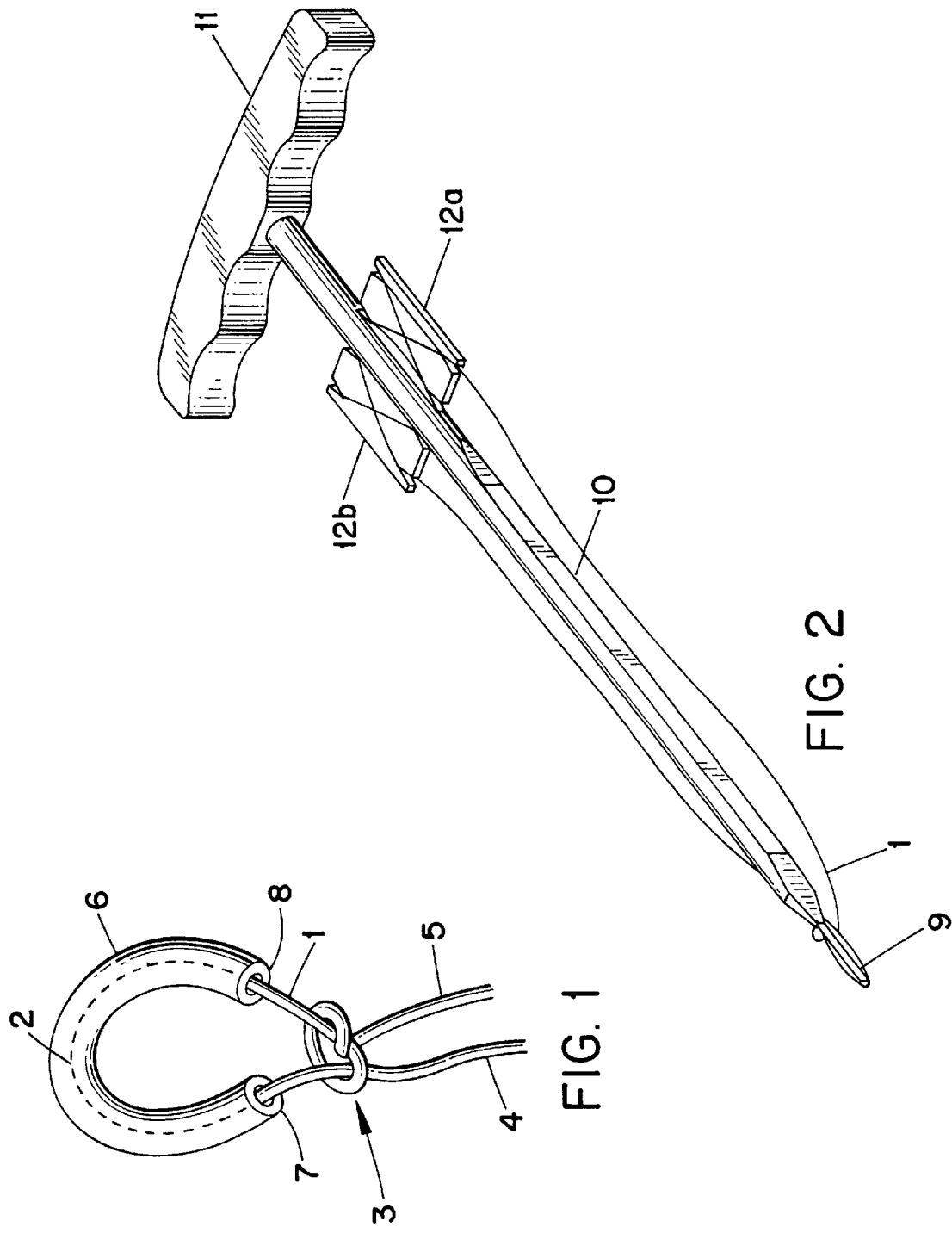

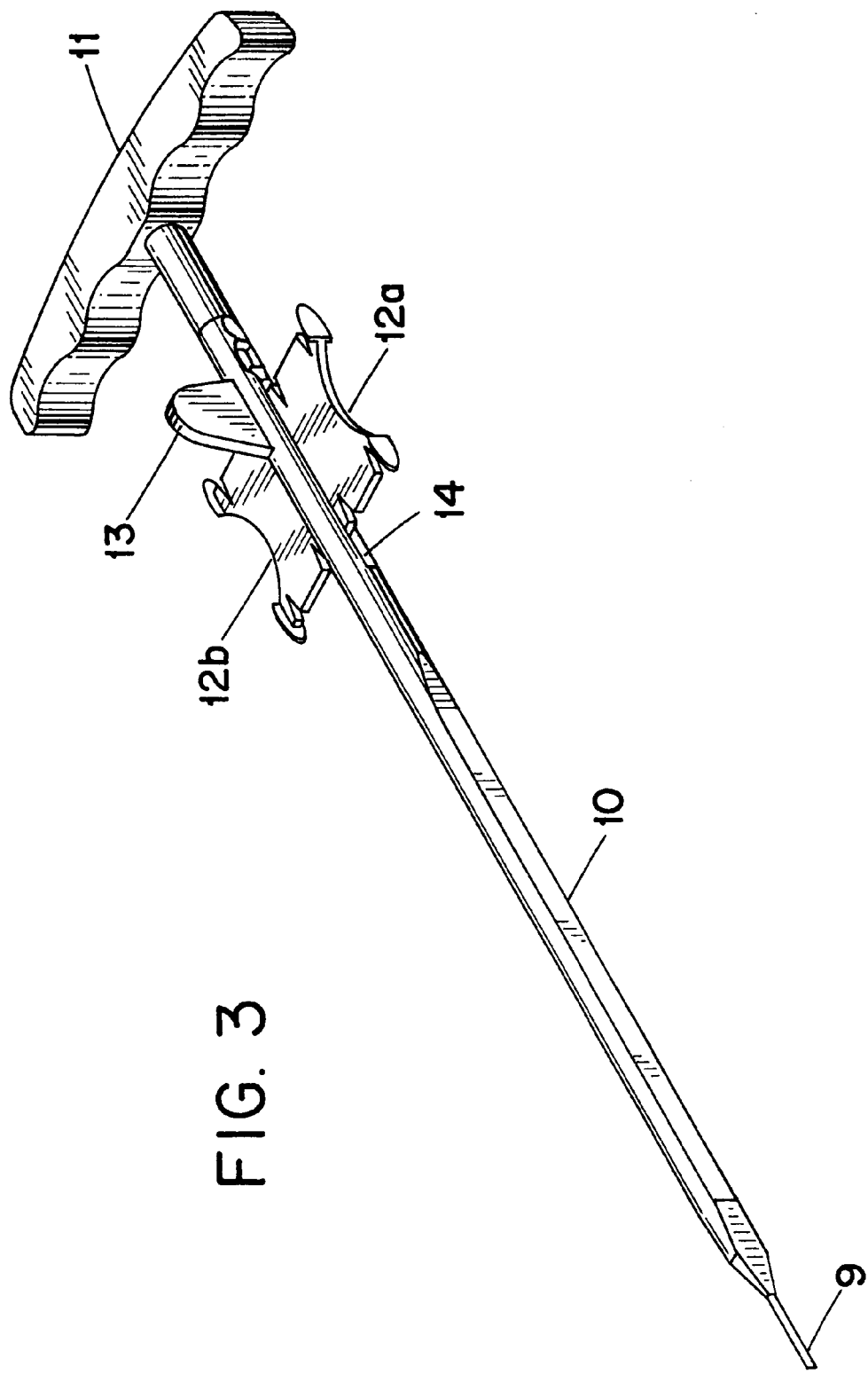

SURGICAL DEVICE FOR ANCHORING IN BONE, AND ANCILLARY FOR INSERTING IT

FIELD OF THE DISCLOSURE

The present invention relates to a surgical device for anchorage in bone, and more particularly to a surgical device that makes it possible to anchor a suture thread or a surgical wire in a bony support, especially in orthopedic, traumatological, gynecological and carcinological surgery.

BACKGROUND OF THE DISCLOSURE

Torn tendons or ligaments are accidents that can befall a great many individuals of all ages, whether they are active or inactive, following trauma or overexertion. The surgical repair techniques commonly used consist of attaching the tendon, using a suture thread, to a screw, a peg or a piton fixed into the neighboring bone.

For that, it is generally necessary to bore a hole in the bone and screw in a screw or a piton, or to bore in the bone an untapped hole that will take a peg that can lock into the bone, which serves as an anchorage means to which a suture thread is then attached and used to attach the tendon which has been torn from its bony support. In other techniques, once a hole adapted to receive an anchoring piton has been bored, the suture thread is passed through the eye of the anchoring piton, then the piton is inserted into the hole using special equipment, and finally the tendon to be attached is stitched on. An example of an anchoring screw for attaching tissues using a suture thread is described in the patent U.S. Pat. No. 5,443,482.

Depending on the case, the interventions may be performed either in open surgery or in closed surgery using coelioscopic or arthroscopic methods. Surgical techniques employing devices of this kind are described for example by F. A. Barber et al., *J. of Arthroscopy and Related Surgery*, vol. 11, no. 1, p. 21–28 (1995).

These known devices have the drawback of being highly invasive, non-absorbable and of requiring insertion techniques which are often tricky to employ; furthermore some products used here contain allergizing materials, for example certain shape-memory materials, and sometimes even cancerogenic materials, according to certain authors. Furthermore, a great many screws, pegs or pitons and accessories for boring the bone and inserting the anchoring means need to be available in various sizes in order to suit all situations.

SUMMARY OF THE DISCLOSURE

The object of the present invention is a device for anchorage in bone needing the prior operation of boring a simple hole with any walls, without requiring tapping, and which allows the attachment of organs such as tendons and ligaments, or the suspending of the neck of the uterus, by means of a surgical wire or a suture thread without it being necessary to use a means of the screw or piton type.

Another object of the invention is ancillary equipment specially adapted for insertion of the aforementioned anchoring device.

The anchoring device in accordance with the present invention can be used in combination with a hole bored in the bony support, and includes a thread or wire comprising a middle part which is intended to be introduced into the hole previously bored, which has a loop shape closed by a running knot, carrying on the loop part a deformable tubular sleeve or jacket which can slide along the thread or wire within the limits of the loop.

According to a preferred embodiment, the thread or wire used is a surgical wire or a suture thread which may or may not be absorbable, the wire or thread may be made, for example, of polyester, such as Ercylene® or of polyamide such as Trynil®.

The tubular sleeve or jacket which can slide along the thread or wire in the loop has an overall length which is less than or equal to twice the depth of the drilling in the bone and a diameter less than or equal to that of the hole bored in the bone. Thus, the loop carrying the sleeve is fully inserted into the hole bored in the bone. This sleeve may advantageously be made of any deformable material, preferably one having a certain amount of elasticity, which has the property of being implantable, which may or may not be absorbable (for example a braided plastic or metal wire, a tube made of polyester or of polyamide, or a tube made of silicone).

Depending on the case, the sleeve may be made of a single element or of several elements. Upon insertion, the ends of the sleeve may butt against the running knot, but they may just as easily be some distance from it, the only proviso being that the thread or wire, when the knot tightens, should come up against the sleeve and cause it to deform.

According to a simple embodiment, the sleeve in the form of a linear cylinder is slipped onto the thread or wire, then the loop is formed around the sleeve.

According to an alternative form of the invention, the wall of the sleeve is pierced in its middle with an orifice through which the two strands of thread or wire pass. Thus the thread or wire enters the sleeve via its middle, leaves it for a first time via one end, forms a loop and enters again via the other end of the sleeve and re-emerges via the orifice made in the middle of the sleeve.

According to another embodiment of the invention, the sleeve is in the form of a toric ring having at least one orifice passing through its wall for the passage of the two strands of thread or wire. In this alternative version, the wire enters the sleeve via the orifice, forms a loop around the inside of the annular sleeve, and re-emerges via the same orifice.

The sleeve is preferably reinforced in the region where the thread or wire enters, that is to say around the periphery of each of its ends, or around the orifice made in its wall, as appropriate. This reinforcement can be obtained for example by providing an extra thickness of material or by attaching a stronger strip by bonding.

The ancillary for inserting the anchoring device in accordance with the present invention comprises a shaft which at one end has a spike that can hold the loop of thread or wire and be introduced into the hole bored in the bone, and at the other end has a handle for manipulation by the user, together with at least one thread- or wire-carrying support secured to the shaft and carrying the ends of the thread or wire.

According to a preferred embodiment, the handle can slide longitudinally with respect to the shaft over a distance which is limited by at least one stop, and the shaft or the handle comprises means for locking their relative position until a predetermined tensile force is applied to the handle or to the shaft.

According to another feature of the present invention, the ancillary comprises two thread- or wire-carrying supports, each consisting of a small plate arranged on the shaft, the two small plates being situated one on either side of the axis of the shaft, and capable of sliding along the shaft over distances which differ from one another. Fixed to the small plate that can slide over the longest distance is the end of the strand of thread or wire carrying the running knot, while the end of the other strand of thread or wire, which does not carry the running knot, is attached to the small plate which is stationary or slides over the shorter distance.

The ancillary for inserting the anchoring device of the invention can be used easily by inserting the spike of the ancillary, carrying the loop and its sleeve, into the hole already bored in the bone, until the loop is fully engaged in the hole. Once the spike has been withdrawn from the hole, leaving the thread or wire and the sleeve in there, all that is required is for tension to be exerted on that strand of the thread or wire that does not carry the running knot, while at the same time slightly holding the other strand still in order to cause the loop to tighten up inside the hole in the bone and the sleeve to deform on the loop until it adopts the shape of a ball, the diameter of which exceeds that of the tubular sleeve before deformation. As the tension is continued until the device locks up, the deformed sleeve is compressed against the internal walls of the cavity.

As indicated above, the device and the insertion ancillary according to the present invention are quite specifically intended for ligament and tendon repair surgery. The invention can also be used in gynecology, for example, for fixing the uterus to the sacrum using a ligament.

The device of the invention is also suited to carcinological surgery, and in this application use is made of a wire which may contain a radioactive substance such as iridium. The wire is placed in the tumor, preferably using a non-absorbable wire; the latter can be used as a marker for secondary ablation of the tumor.

Tests conducted with the anchoring device according to the present invention, carried out under experimental conditions, have revealed excellent properties of attachment and resistance to pulling out, comparable with those of the best known devices of the state of the art. Using an absorbable braided polyglatine suture thread 0.4 mm in section, with, at the loop, a non-absorbable braided polyester sleeve 0.6 mm in section, inserted into a series of holes 1.6 mm in diameter and 18 mm deep bored in a fresh sheep femur from an abattoir, the resistance to pulling-out along the axis of the hole was about 12 kg. In every instance the suture thread was seen to break without the sleeve being pulled out of the hole.

The features and advantages of the present invention will become more evident in the following examples which relate to preferred embodiments, with reference to the appended drawings, which depict:

BRIEF DESCRIPTION OF DRAWINGS

FIG. 1 is a diagrammatic view of an attachment thread or wire in accordance with the present invention, FIG. 2 is a perspective view of simplified ancillary hardware for inserting the anchoring device of FIG. 1;

FIG. 3 is a perspective view of ancillary hardware which is improved over that of FIG. 2, allowing semiautomatic insertion of an anchoring device according to FIG. 1.

Figure 4A:
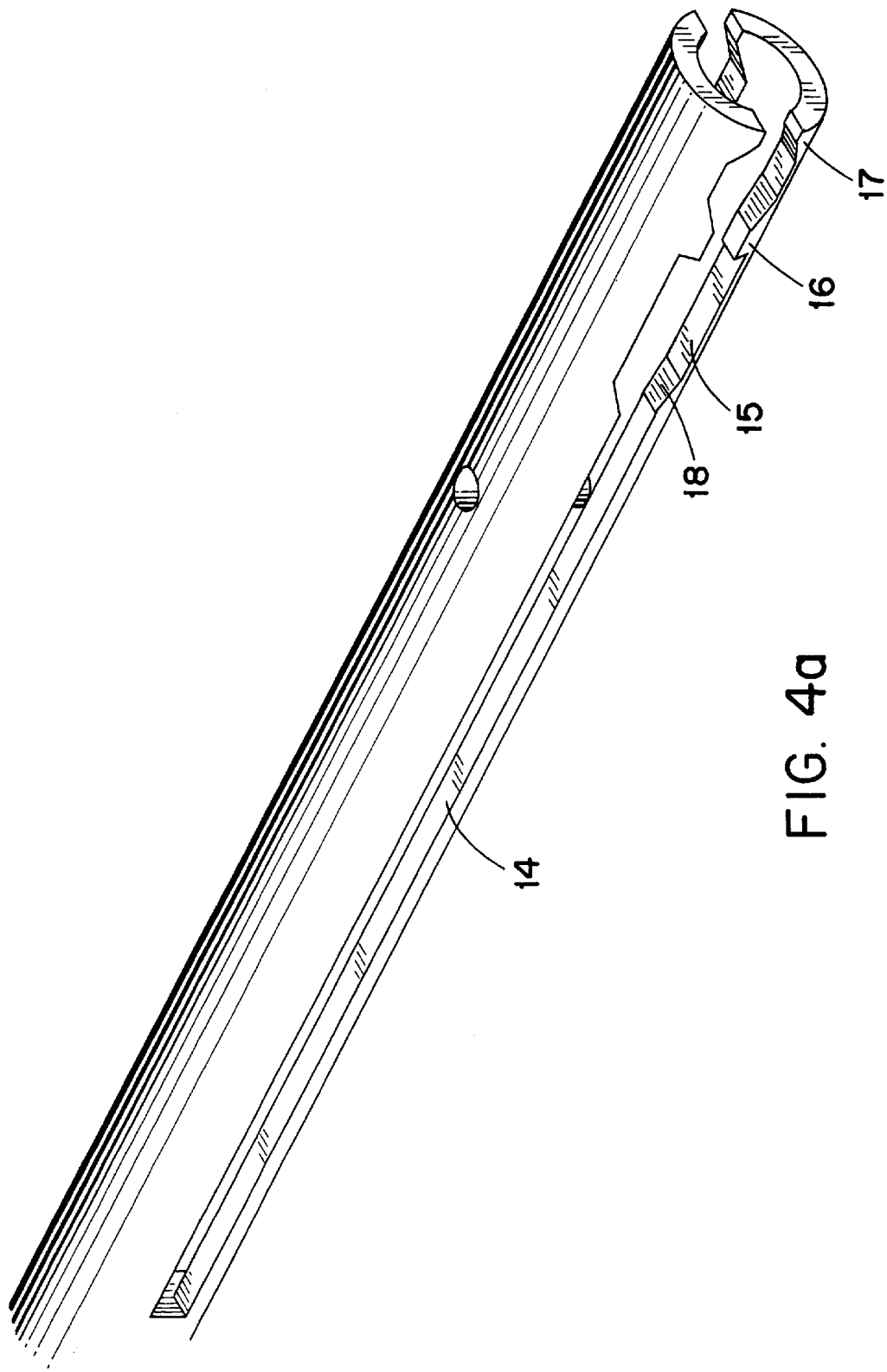
FIGS. 4a and 4b provided detail, there of of the shaft of the hardware of FIG. 3; and of the handle that can be inserted in it.
Figure 4B:
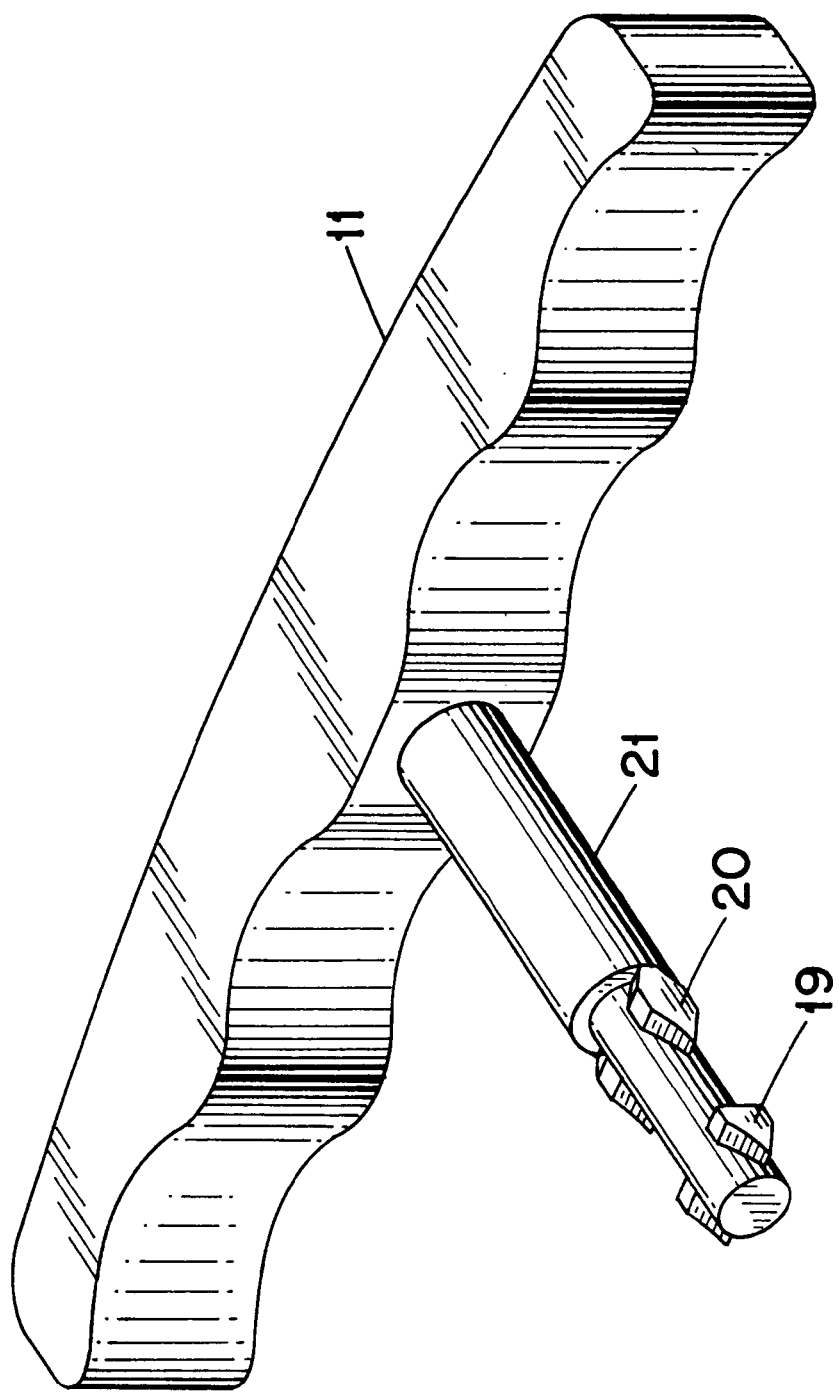

As FIG. 1 shows, the anchoring device of the present invention comprises a suture thread (1) which at its middle part forms a loop (2) closed by a running knot (3) that can be tightened simply by pulling on one of the two strands (4, 5) of the thread (1).

Within the loop (2), the thread (1) is jacketed with a deformable and compressible sleeve (6) capable of sliding along the thread. Tension on the strand (4) of the thread causes a reduction in the length of the loop (2) until its length becomes equal to that of the sleeve (6). By continuing to exert tension on the strand (4) of the thread (1), on the one hand, the sleeve is compressed and its surface begins to wrinkle on account of the compressibility of the material of which it is made, and on the other hand, the knot (3) begins to tighten. The edges of the sleeve, at each of its ends (7) and (8), are reinforced to prevent them from being cut by the suture thread when the latter is tightened. This reinforcement is obtained here simply by increasing the thickness of material.

The device is inserted using ancillary hardware like that described below. The insertion method consists in introducing the loop (2) carrying the sleeve (6) into the hole bored in the bone, then in tightening by exerting tension on the strand (4) of the thread (1). It is preferable for the entire loop together with the running knot (3) to be inserted in the hole.

When the running knot (3) is tightened by pulling on the strand (4) of the thread, the loop is tightened up and the flexible sleeve (6) is compressed inside the hole. Then, by tightening further by pulling on the strand (4) of the thread (1), the sleeve (6) is deformed until it adopts the shape of a ball. This ball will be unable to come back out of the hole through which it was inserted into the bone because its diameter has become markedly larger than that of the bored hole. What is more, this ball bears on the internal face of the cortical bone or in the spongy bone if it is hard enough.

All that is required therefore is for a suture thread to be chosen that carries a sleeve which has a length and diameter which, when the running knot (3) is tightened, leads to the formation of a ball which will bear on the hard internal face of a bone and the diameter of which will be large enough to withstand the loadings applied to it.

The anchoring device described hereinabove is inserted efficiently using ancillary hardware in accordance with the invention, depicted in FIG. 2.

Depicted in this figure is simple ancillary hardware that makes the insertion of the anchoring device in a hole already bored in a bone easier.

This ancillary comprises a spike (9) intended to support the loop of suture thread (1) so that it can be inserted into the hole bored in the bone (not depicted). This spike (9) is fixed to a shaft (10) secured to a handle (11). Arranged on the shaft (10) close to the handle (11) are two small plates (12a) and (12b) over which the two ends of the suture thread (1) are placed to make them easier for the user to manipulate.

Once the hole has been bored in the bone using conventional equipment, the spike (9) bearing the thread (1) formed into a loop and carrying its sleeve (6) is introduced into the hole, then the strands (4) and (5) of the thread (1) which are fixed to the small plates (12a) and (12b) are undone. The ancillary is withdrawn from the hole by acting on the handle (11), then the strand (4) of the thread (1) is pulled to make the running knot (3) run and to make the sleeve (6) deform so that it forms a ball.

The ancillary depicted in FIG. 3 comprises a spike (9), a shaft (10), a handle (11) and small plates (12a) and (12b) which are identical to those of FIG. 2, but the handle and the small plates may move axially with respect to the shaft.

A removable pin (13) allows the two thread- or wire-carrying small plates (12a) and (12b) to be locked, while the handle is held in place on the shaft by simple snap-fitting. The shaft (10) is split by a slot (14) which allows the small plates to move when the pin (13) is removed. This slot (14) is longer on the side of the small plate (12b) than it is on the side of the small plate (12a), so as to restrict the movement of the small plates differentially, as indicated below, the translational movement of the small plate (12b) being able to occur over a longer distance than that of the small plate (12a). Thus, the strand of thread or wire forming the knot is fixed to the small plate whose movement is the greatest.

As FIG. 4a shows, the slot (14) is widened in the part (15) that accommodates the handle. This widened part (15) of the slot has a stop (16) and is bounded by the two shoulders (17) and (18) formed on each half of the shaft. This stop and these shoulder are intended to interact with two studs (19) and (20) provided on the stem (21) of the handle (11).

When the handle is in place, its stem (21) is inserted inside the shaft (10) until the stud (19) comes to bear against the shoulder (18), the stud (20) then bearing against the inclined part of the stop (16).

The head of the stud (19) is triangular in shape, the point facing toward the bottom of the slot (14), while its base faces toward the handle (11). By contrast, the stud (20) has a head with a hexagonal shape. Thus, when the handle (11) previously installed on the shaft (10) is pulled hard enough, the stud (20), on account of its shape, can pass over the stop (17) by parting the two branches of the shaft (10) on either side of the slot (14), the movement being restricted by the stud (19), the base of which comes against the stop (16). In this position, the stud (20) has passed over the shoulder (17).

This movement of the handle (11) relative to the shaft (10) can be achieved only by exerting a predetermined tensile force on the handle, so as to overcome the resistance of the stop (17) against one of the hexagon faces of the stud (20) and to force the two branches of the shaft to part on either side of the slot (14). Thus, gentle tension on the handle (11) draws the shaft (10) along with the handle, whereas stronger tension detaches the handle from the shaft.

The anchoring device is inserted using the ancillary hardware of FIG. 3 in a semi-automatic way as described below.

The anchoring device is first of all inserted into a hole already bored into the bone. For this, the closed loop carrying the flexible sleeve is placed on the spike (9) and the ends of the suture thread are fixed to the thread-carrying small plates (12a) and (12b) like in the previous example, the two strands of thread being stretched between the spike and each small plate.

The spike carrying the thread is introduced into the hole bored in the bone and the pin (13) is removed in order to release the two small plates which can slide along the shaft (10). The user pulls gently on the handle, and this allows the spike to be withdrawn from the hole, the handle and the shaft remaining attached. At the same time, the loop, its sheath and the knot remain in the hole because of frictional forces. Then, given that the small plates can slide along the shaft (10), the small plate (12a) will come up against the bottom of the slot (14) and will tension the strand (4). This will cause the knot (3) to tighten and the sleeve (6) to deform until it forms a ball. If the user continues to pull on the handle, above and beyond a predetermined value, the tensile force will exceed the resistance put up by the stop (17) on the hexagonal stud (20) and the handle will then slide with respect to the shaft until the triangular stud (19) comes up against the stop (16). This makes it possible to adjust the force to be exerted on the strand (4) to ensure anchorage of the sleeve (6) which has become a ball, and the fact that the stud (15) comes up against (16) stops the shaft (10) from falling.

Figure 5:
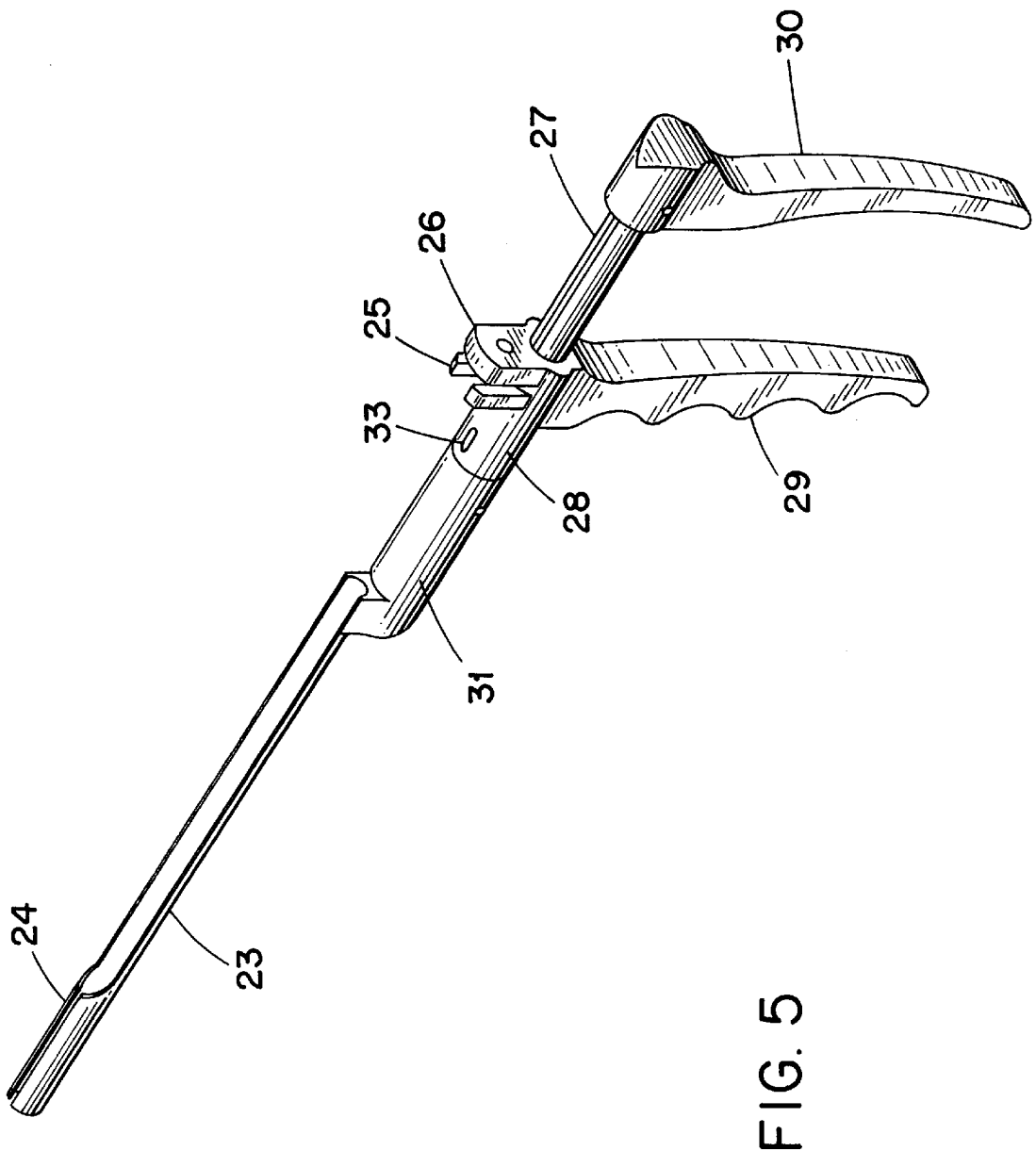
FIG. 5 is a view of a support element that can accommodate the element of FIG. 6, similar to that of FIG. 3; for automatic insertion.
Figure 6:
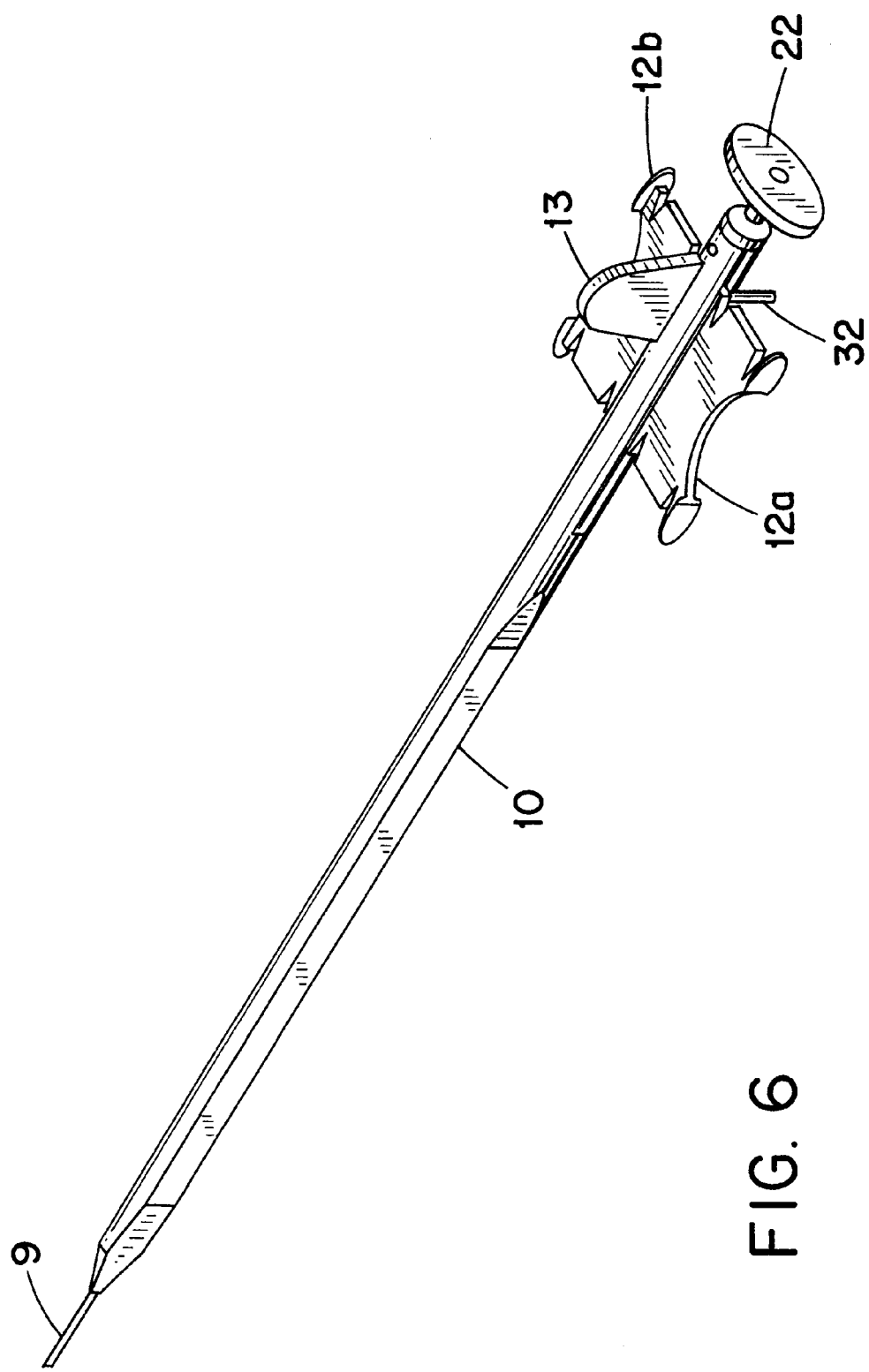
FIG. 6: a view of the element that combines with that of FIG. 5 for the automatic insertion of the anchoring device.

The ancillary hardware whose two constituent parts are depicted in FIGS. 5 and 6 is intended for automatic insertion of the anchoring device of the invention, it being possible in this case for the user to operate the ancillary with just one hand.

The part in FIG. 5 is a support that accommodates the part in FIG. 6. The latter part is similar to the ancillary hardware in FIG. 3, the handle (11) being replaced by a plunger (22).

The support part in FIG. 5 comprises a semi-cylindrical support (23) intended to accommodate the shaft (10) of the part in FIG. 6. To ensure that the shaft is held correctly, this support is closed at its distal end (24). Thus the other part is inserted by introducing the end of the shaft (10) carrying the spike (9) into the open part of the support (23) and by sliding it into the closed part (24) until the plunger (22) comes up between the two stops (25) and (26) which are part of the support.

That part (28) of the support carrying the stops (25) and (26) can slide along the stem (27), sliding movement being achieved by acting on the handle (29) secured to the support (28) and on the handle (30) secured to the stem (27) (the two handles are kept apart by a spring which has not been depicted). The end of the stem (27) is secured to that part (31) of the support which carries the open tube (23). When the pin (13) is in place, its shank (32) engages in the hole (33) made in the support (28) and the stem (27) and thus the two handles are blocked one with respect to the other.

The user grasps hold of the ancillary, comprising the two parts of FIGS. 5 and 6 assembled, by the two handles (29) and (30), using just one hand, he engages the spike (9) bearing the loop and the sleeve into the hole already bored in the bone, then he removes the pin (13) thus freeing the handles (29) and (30). By acting on the handles in such a way as to bring them closer together, he causes a movement of withdrawing the shaft (10) which slides in the semicylindrical support (23) causing the small plate (12a) to slide with respect to the shaft (10) until it comes up against the bottom of the slot (14), then the strands (4) goes taut and causes the knot (3) to tighten and the sleeve (6) to turn into a ball. The user needs to continue to squeeze the handles until the plunger (22) breaks at its narrowing. This lets the user know that he has exerted the force needed to insert the anchoring system.

Figure 7:
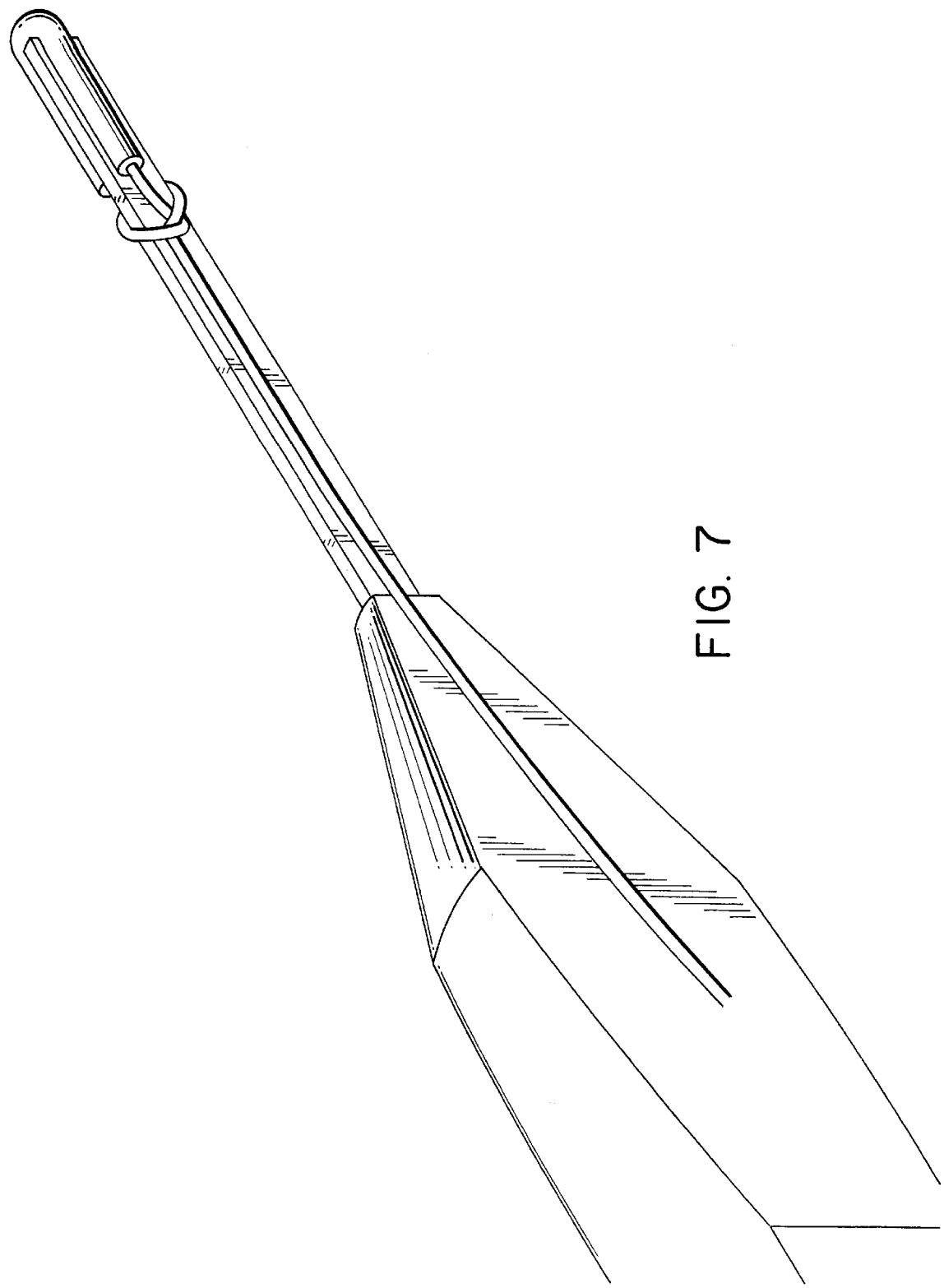
FIG. 7: a detail view showing the position of the thread or wire and of the sleeve of the anchoring device on the spike of ancillary hardware like that depicted in the above figures.

FIG. 7 explicitly shows the position of the suture thread (1) at the closed loop and carrying the flexible sleeve (3) in place on the spike (9) at the end of the shaft (10) of the insertion ancillary.

I claim:

1. A surgical device suitable for anchorage of a thread or wire to a bone having a hole bored therein, said device consisting essentially of:

a thread or wire in the form of a loop having a running knot; and a deformable tubular sleeve carried by the thread or wire, said sleeve sliding along the thread or wire within the limits of the loop.

2. The device according to claim 1, wherein the sleeve is in the form of a loop by tension exerted on at least one strand of the thread or wire.

3. The device according claim 2, wherein the length of the sleeve is less than or equal to twice the depth of the hole bored in the bone.

4. The device according to claim 1, wherein the diameter of the sleeve is less than or equal to the diameter of the hole.

5. The device according to claim 1, wherein the sleeve is made of at least one single linear cylindrical element.

6. The device according to claim 5, wherein the sleeve is made of a single linear cylindrical element open at both ends.

7. The device according to claim 5, wherein the sleeve comprises at least one orifice passing through its wall for the passage of two strands of thread or wire.

8. The device according to claim 5, wherein the sleeve is made of a toric ring having at least one orifice passing through its wall for the passage of two strands of thread or wire.

9. An ancillary in combination with an anchoring device useful for anchorage of a thread or wire to a bone having a hole bored therein, the combination comprising:

an anchoring device having a thread or wire in the form of a loop and having a running knot and ends, and a deformable tubular sleeve carried by the thread or wire, said sleeve sliding along said thread or wire within the limits of the loop; and a shaft which at a first end has a spike having a distalmost end that receives and holds said sleeve and said loop of thread or wire to be introduced into the hole bored in the bone on said distalmost end, said shaft including a handle for manipulation by the user at a second end opposite said spike, and at least one thread- or wire-carrying support secured to the shaft and carrying the ends of the thread or wire.

10. An ancillary for inserting an anchoring device including a thread or wire in the form of a loop having a running knot and a deformable tubular sleeve carried by the thread or wire, said sleeve sliding along the thread or wire within the limits of the loop, the ancillary comprising:

a shaft which at one end has a spike that can hold the loop of thread or wire to be introduced into the hole bored in the bone and at the other end has a handle for manipulation by a user;

at least one thread- or wire-carrying support secured to the shaft for carrying the ends of the thread or wire;

wherein the handle can slide longitudinally with respect to the shaft over a distance which is limited by at least one stop, and the shaft or the handle comprises a device for locking the relative position of the handle or shaft until a predetermined tensile force is applied to the handle or to the shaft.

11. An ancillary for inserting an anchoring device including a thread or wire in the form of a loop having a running knot and a deformable tubular sleeve carried by the thread or wire, said sleeve sliding along the thread or wire within the limits of the loop, the ancillary comprising:

a shaft which at one end has a spike that can hold the loop of thread or wire to be introduced into the hole bored in the bone and at the other end has a handle for manipulation by a user;

at least one thread- or wire-carrying support secured to the shaft for carrying the ends of the thread or wire;

wherein the ancillary comprises two thread- or wire-carrying supports, each including a small plate arranged on the shaft, the two small plates being situated one on either side of the axis of the shaft, and being capable of sliding along the shaft over distances which differ from one another.

12. The ancillary according to claim 11, wherein the end of the strand of thread or wire carrying the running knot is fixed to the small plate that can slide over the longest distance, while the end of the other strand of thread or wire, which does not carry the running knot, is attached to the small plate which is stationary or slides over a shorter distance.

* * * * *